United States Patent
Blyakher et al.

(10) Patent No.: US 8,782,832 B2
(45) Date of Patent: Jul. 22, 2014

(54) SYSTEM, METHOD, AND APPARATUS FOR PATIENT POSITIONING TABLE

(75) Inventors: Arkady Blyakher, New York, NY (US); John Denneen, Somers, NY (US); Howard J. Hillstrom, Staten Island, NY (US); Andrew Phillip Kraszewski, Brooklyn, NY (US); Mark William Lenhoff, New York, NY (US); Roger Franklin Widmann, Scarsdale, NY (US); Helene Pavlov, New York, NY (US); Edward T. White, Sayreville, NJ (US); Mary Campolongo, Glen Oaks, NY (US)

(73) Assignee: New York Society for the Ruptured and Crippled Maintaining the Hospital for Special Surgery, New York, NY (US)

( * ) Notice: Subject to any disclaimer, the term of this patent is extended or adjusted under 35 U.S.C. 154(b) by 616 days.

(21) Appl. No.: 12/939,341

(22) Filed: Nov. 4, 2010

(65) Prior Publication Data
US 2011/0170671 A1    Jul. 14, 2011

Related U.S. Application Data

(60) Provisional application No. 61/259,045, filed on Nov. 6, 2009.

(51) Int. Cl.
*A47B 13/00*    (2006.01)

(52) U.S. Cl.
USPC .............. 5/601; 5/621; 5/623; 5/624; 5/646; 5/648

(58) Field of Classification Search
USPC .............. 5/601, 621, 623, 624, 646, 648; 378/209
See application file for complete search history.

(56) References Cited

U.S. PATENT DOCUMENTS

| | | | | |
|---|---|---|---|---|
| 1,697,121 | A * | 1/1929 | Knebel | 602/39 |
| 2,693,987 | A * | 11/1954 | Wall et al. | 5/609 |
| 3,389,702 | A * | 6/1968 | Kennedy | 606/119 |
| 3,829,079 | A * | 8/1974 | Fox | 5/621 |
| 4,143,652 | A * | 3/1979 | Meier et al. | 600/203 |
| 4,526,355 | A * | 7/1985 | Moore et al. | 5/624 |
| 5,077,780 | A * | 12/1991 | Lee, Jr. | 378/196 |
| 5,131,106 | A * | 7/1992 | Jackson | 5/613 |
| 5,390,383 | A * | 2/1995 | Carn | 5/624 |
| 5,400,772 | A * | 3/1995 | LeVahn et al. | 600/230 |
| 5,810,006 | A * | 9/1998 | Votruba et al. | 600/415 |
| 6,023,800 | A * | 2/2000 | Stickley | 5/621 |
| 6,108,841 | A * | 8/2000 | Cameron et al. | 5/648 |
| 6,260,220 | B1 * | 7/2001 | Lamb et al. | 5/607 |
| 6,311,349 | B1 * | 11/2001 | Kazakia et al. | 5/624 |
| 6,499,158 | B1 * | 12/2002 | Easterling | 5/600 |
| 6,671,904 | B2 * | 1/2004 | Easterling | 5/601 |
| 6,820,621 | B2 * | 11/2004 | DeMayo | 128/845 |
| 6,941,951 | B2 * | 9/2005 | Hubert et al. | 128/845 |
| 7,159,832 | B2 * | 1/2007 | Easterling | 248/316.6 |

(Continued)

*Primary Examiner* — Robert G Santos
*Assistant Examiner* — David E Sosnowski
(74) *Attorney, Agent, or Firm* — Leason Ellis LLP (57) ABSTRACT

An approach is provided for patient positioning. A patient is arranged on a table having a positioning assembly coupled thereto, the positioning assembly including a plurality of spatially configurable members. A spatial configuration of at least one of the plurality of spatially configurable members is arranged to support the patient in a multipoint bending position during a medical procedure.

14 Claims, 9 Drawing Sheets

(56) References Cited

U.S. PATENT DOCUMENTS

| | | | |
|---|---|---|---|
| 7,246,390 B2* | 7/2007 | Mitsuishi et al. | 5/648 |
| 7,316,040 B2* | 1/2008 | Siccardi et al. | 5/621 |
| 7,395,563 B2* | 7/2008 | Whitmore et al. | 5/601 |
| 7,600,281 B2* | 10/2009 | Skripps | 5/621 |
| 7,832,035 B2* | 11/2010 | Walczyk | 5/648 |
| 8,020,228 B2* | 9/2011 | Rao et al. | 5/621 |
| 8,256,047 B2* | 9/2012 | Klemm et al. | 5/621 |
| 8,286,283 B2* | 10/2012 | Copeland et al. | 5/621 |
| 8,302,228 B2* | 11/2012 | Aboujaoude | 5/648 |
| 8,322,342 B2* | 12/2012 | Soto et al. | 128/845 |
| 8,510,882 B2* | 8/2013 | Campagna et al. | 5/621 |
| 2004/0123389 A1* | 7/2004 | Boucher et al. | 5/623 |
| 2006/0185090 A1* | 8/2006 | Jackson | 5/621 |
| 2007/0089239 A1* | 4/2007 | Whiteside | 5/624 |
| 2008/0009713 A1* | 1/2008 | Tuma | 600/424 |
| 2008/0034502 A1* | 2/2008 | Copeland et al. | 5/621 |
| 2008/0054698 A1* | 3/2008 | Klemm et al. | 297/316 |
| 2010/0018537 A1* | 1/2010 | Soto et al. | 128/845 |
| 2010/0192301 A1* | 8/2010 | Di Lauro | 5/621 |
| 2010/0242177 A1* | 9/2010 | Malcolm et al. | 5/621 |

\* cited by examiner

FIG. 12

SYSTEM, METHOD, AND APPARATUS FOR PATIENT POSITIONING TABLE

CROSS REFERENCE TO RELATED APPLICATIONS

The present application claims the benefit of U.S. patent application Ser. No. 61/259,045, filed Nov. 6, 2009, which is hereby incorporated by reference in its entirety.

BACKGROUND

Assessment of curve flexibility (or elasticity) is a critical step in determining the structural nature of a deformity, as well as in planning for surgical correction. For instance, idiopathic scoliotic curves are often evaluated, diagnosed, and treated based, at least, on information learned from one or more radiographic images obtained when maximum feasible traction is applied to the idiopathic scoliotic curves without harming a subject (or patient). These radiographic images typically include multiple "bending films" that are exposed while the structural deformity is flexed or otherwise bent. As such, acquiring a bending film requires a patient, or a selected portion of the patient's body, to be forcibly positioned and, thereby, constrained in one or more orientations during radiographic imaging. Unfortunately, conventional patient tables have inadequately met the needs of arranging and supporting a patient in certain medically relevant positions, such as multipoint bending positions. For instance, conventional patient tables require one or more administrative assistants, doctors, technicians, or other personnel to physically arrange and hold the patient in a required multipoint bending position while the radiographic images are acquired, which exposes these individuals to unnecessary radiographic radiation.

Therefore, there is a need for cost-effective, patient positioning equipment and techniques that are capable of supporting a patient in one or more medically relevant positions.

BRIEF DESCRIPTION OF THE DRAWINGS

Various exemplary embodiments are illustrated by way of example, and not by way of limitation, in the figures of the accompanying drawings in which like reference numerals refer to similar elements and in which.

DESCRIPTION OF CERTAIN EMBODIMENTS

A preferred apparatus, method, software, and system for arranging and supporting a patient in one or more medically relevant positions are described. In the following description, for the purposes of explanation, numerous specific details are set forth in order to provide a thorough understanding of the preferred embodiments of the invention. It is apparent, however, that the preferred embodiments may be practiced without these specific details or with an equivalent arrangement. In other instances, well-known structures and devices are shown in block diagram form in order to avoid unnecessarily obscuring the preferred embodiments of the invention.

Although various exemplary embodiments are described with respect to performing radiographic studies, it is contemplated that various exemplary embodiments are also applicable to facilitating other diagnostic studies, such as computed tomography (CT) studies, fluoroscopic studies, magnetic resonance imaging (MRI) studies, positron emission tomography studies (PET), single photon emission computed tomography (SPECT) studies, and the like.

Figure 1:
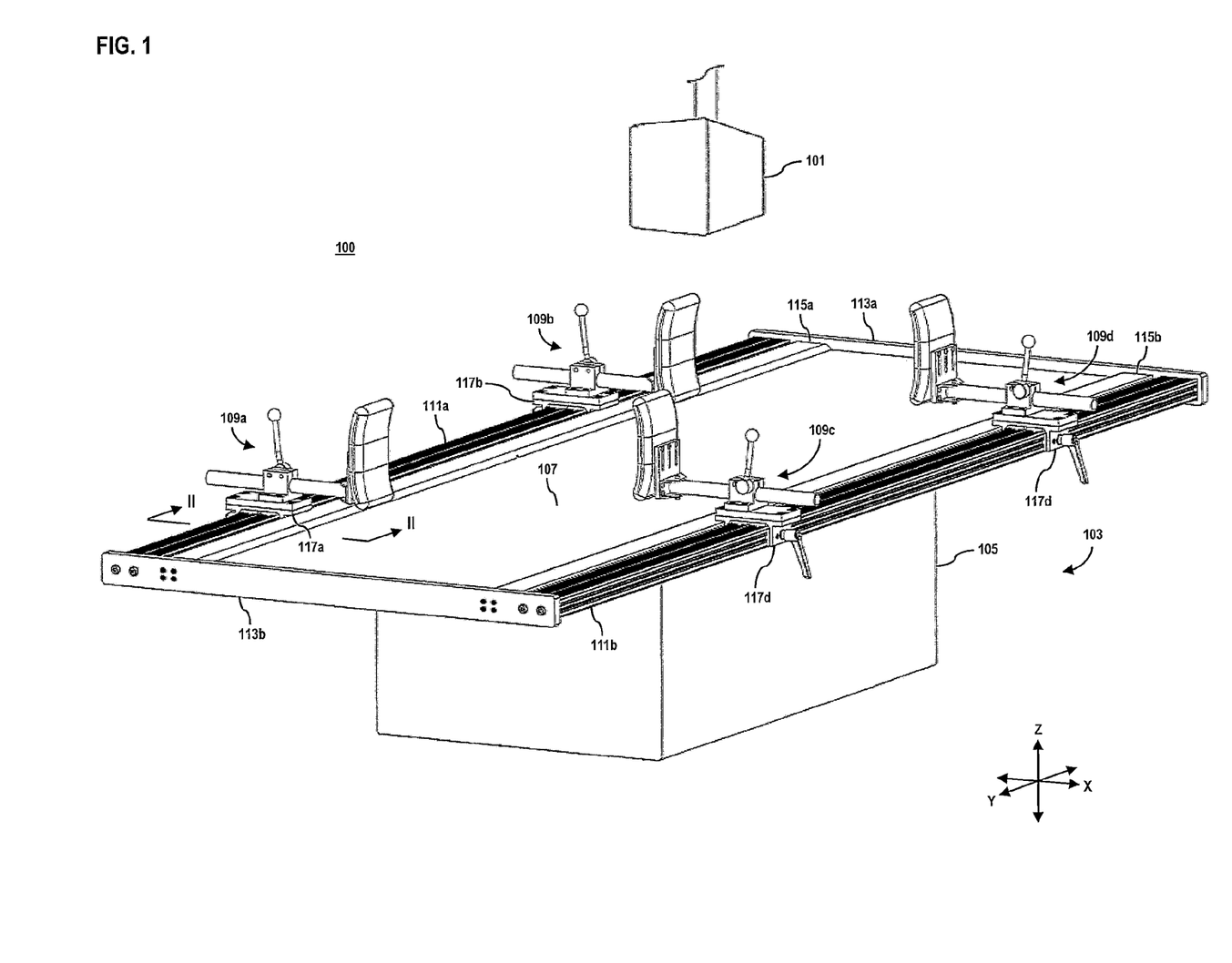
FIG. 1 is a perspective view of a diagnostic system including a patient table, according to an exemplary embodiment.

FIG. 1 is a perspective view of a diagnostic system including a patient table, according to an exemplary embodiment. For illustrative purposes, diagnostic system (or system) 100 is described as a diagnostic radiographic system configured to obtain radiographic images (or radiographs) of a subject or patient (not shown). In this manner, system 100 may be implemented as a tool for assessing and diagnosing structural deformities, such as idiopathic scoliotic curves, as well as numerous other conditions, whether structurally related or not. As such, system 100 includes a radiographic tube (or camera) 101 and a patient table 103 having a base member 105 fixedly coupled to a top member (or tabletop) 107. According to exemplary embodiments, patient table 103 includes a positioning assembly that has a plurality of spatially configurable positioning members (e.g., spatially configurable bolsters 109a, 109b, 109c, and 109d) which, when arranged, are configured to support a subject in a variety of different medically relevant positions (e.g., multipoint bending positions, such as three-point, four-point, etc., bending positions) during a medical procedure, such as, for example, a radiographic imaging procedure. In this manner, the positioning assembly of system 100 may be (or may include) any suitable mechanism(s) that can be spatially configured according to one or more degrees of freedom and, thereby, to enable a subject to be arranged and supported in one or more medically relevant positions. While specific reference will be made hereto, it is contemplated that system 100 may embody many forms and include multiple and/or alternative components.

Traditionally, "bending films" have been acquired by several physicians manually arranging a patient's body in a multipoint (e.g., three-point, four-point, etc.) bending position that is then maintained by these individuals during a radiographic exposure period. At least in the case of diagnosing and treating scoliosis, radiographic images are obtained over the length of a body of the patient and, therefore, even if these individuals wear protective vests, the remainder of their bodies is still unduly exposed to otherwise harmful radiation. As such, the approach according to certain exemplary embodiments of system 100 stems from the recognition that providing new equipment and techniques to arrange and support a patient in one or more medically relevant positions that do not require individuals to physically hold the patient in such positions while radiographs are being acquired would prevent these individuals from being unnecessarily exposed to otherwise harmful radiographic rays.

As seen in FIG. 1, spatially configurable positioning members (hereinafter "bolsters") 109a-109c that may be supported by one or more guide members, e.g., guide members 111a and 111b, fixedly attached to patient table 103 via, for instance, one or more structural (or cross) members 113a and 113b. Guide members 111a and 111b extend along at least a portion of a longitudinal length of patient table 103, however, it is contemplated that guide members 111a and/or 111b may extend along at least a portion of a transverse width of patient table 103 or any other suitable dimension. In the depicted embodiment, guide members 111a and 111b extend along an entirety of the longitudinal length of patient table 103 and, thereby, are fixedly attached to distal ends of patient table 103 via structural members 113a and 113b. For example, guide members 111a and 111b may be fastened to structural members 113a and 113b that are, in turn, fastened to tabletop 107 at distal ends of side members 115a and 115b. While not illustrated, one or more additional (or alternative) structural supports, e.g., anchors, brackets, plates, protrusions, supports, etc., may be utilized that provide load-bearing characteristics. It is also contemplated that guide members 111a and 111b may be integrally formed to patient table 103; however, in the depicted embodiment, the positioning assembly may be retrofitted to an existing patient table 103 of an existing medical system.

According to exemplary embodiments, bolsters 109a-109d may slidably interface with respective guide members 111a and 111b via guide blocks (or guides) 117a, 117b, 117c, and 117d. For example, bolsters 109a and 109b slidably interface with guide member 111a via respective guides 117a and 117b, whereas bolsters 109c and 109d slidably interface with guide member 111b via guides 117c and 117d, respectively. In this manner, guide member 111a in conjunction with guides 117a and 117b forms, for instance, a first linear bearing assembly and guide member 111b in conjunction with guides 117c and 117d forms, for example, a second linear bearing assembly. The first and second linear bearing assemblies enable bolsters 109a-109d to be linearly displaced (or translated) and, thereby, spatially configured along at least a portion of the longitudinal length of patient table 103, such as linearly displaced in directions parallel (or substantially) parallel to an imaginary Y axis. As previously mentioned, other bolsters (not shown) may interface with other dimensions of patient table 103 thus enabling additional (or alternative) modes of linear displacement, such as linear displacement along a transverse width of patient table 103. Even though limited numbers of bolsters, guides, and guide members are illustrated, it is contemplated that system 100 may include any suitable number or configuration of these components. An exemplary bolster is described in more detail in accordance with FIGS. 2-4, whereas an exemplary guide and corresponding guide member is more fully explained in conjunction with FIGS. 5 and 6. A more in depth description of an illustrative structural member is provided in association with FIG. 7.

Figure 2:
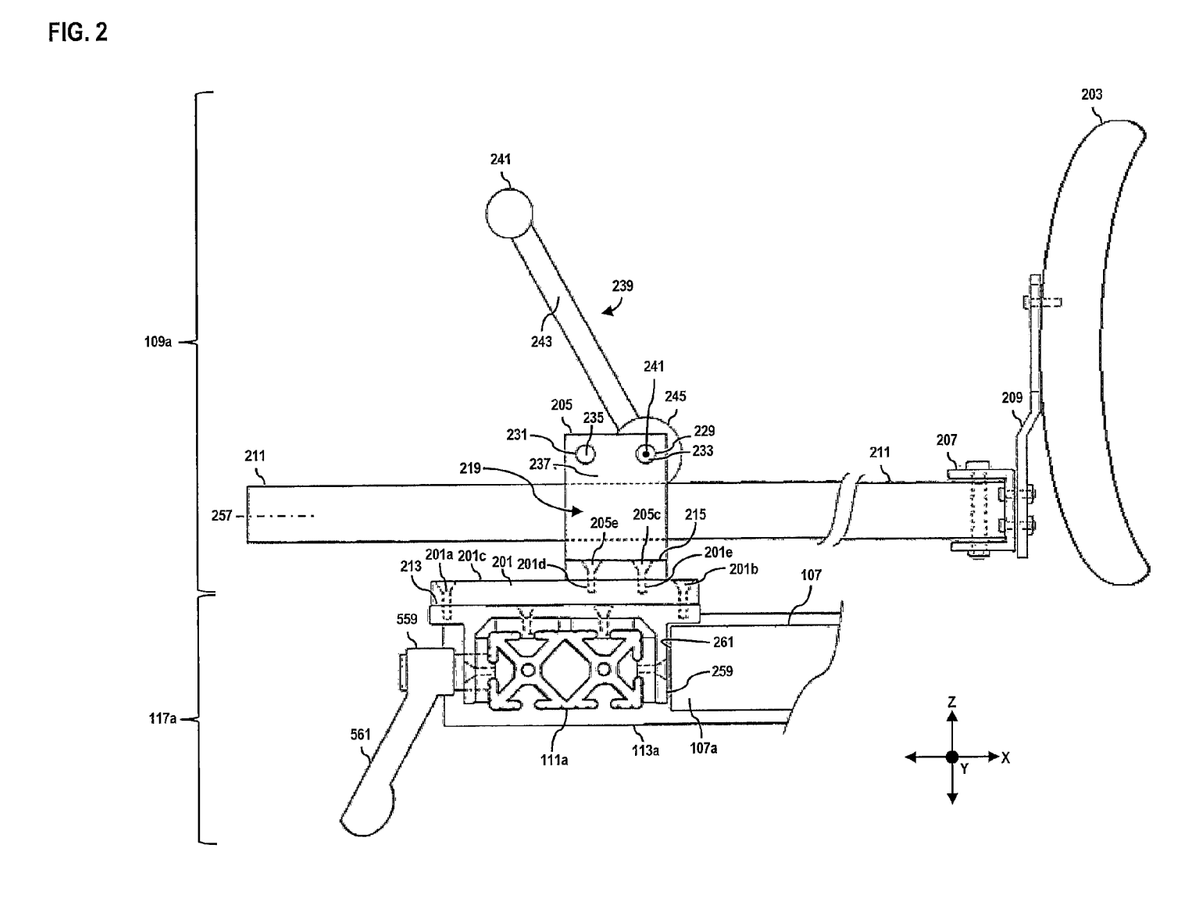
FIG. 2 is an enlarged sectional view of the patient table of FIG. 1 taken along line II-II, according to an exemplary embodiment.

FIG. 2 is an enlarged sectional view of the patient table of FIG. 1 taken along line II-II, according to an exemplary embodiment. As seen in the illustrated embodiment, bolster 109a includes base member 201, bolster pad 203, clamp member 205, first bracket 207, second bracket 209, and telescopic member 211. Bolster 109a may be detachably coupled to an upper surface 213 of guide 117a that, in turn, slidably interfaces with guide member 111a. In this manner, base member 201 may include one or more mounting bores, such as mounting bores 201a and 201b, that enable base member 201 to be, for instance, fastened (e.g., screwed, bolted, pinned, etc.) to guide 117a. According to exemplary embodiments, base member 201 may include four of these mounting bores, which may have tapered (or otherwise countersunk) openings downwardly extending from an upper surface 201c of base member 201 to enable corresponding fasteners (not shown), once engaged with base member 201 and guide 117a, to have upper surfaces that are flush (or substantially flush) with upper surface 201c. It is also noted that these mounting bores may or may not be tapped (or threaded).

Figure 3:
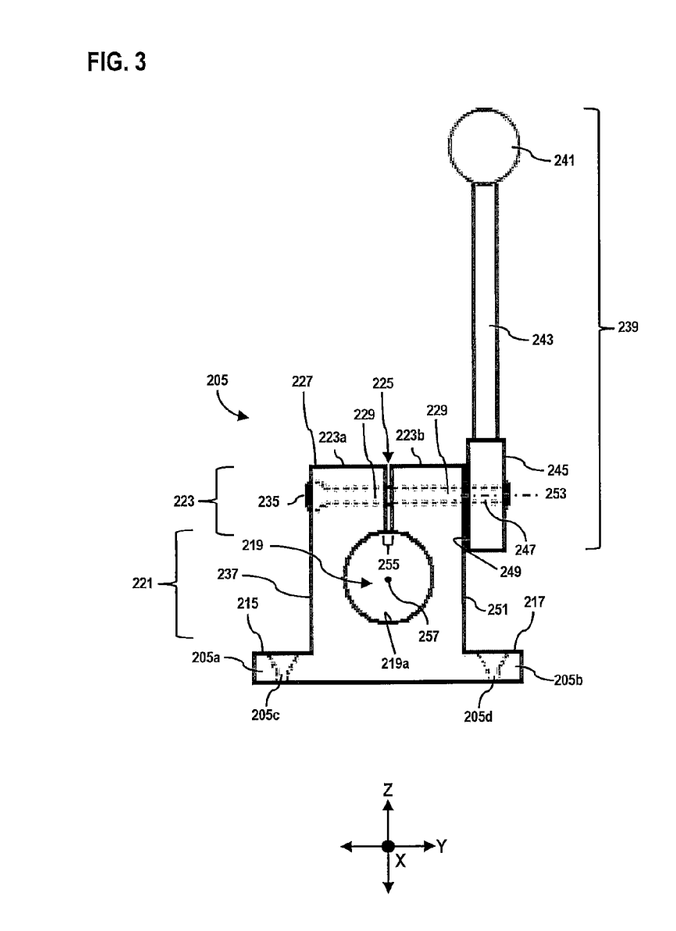
FIG. 3 is an enlarged elevation view of a clamp member of a spatially configurable bolster of the patient table of FIG. 1, according to an exemplary embodiment.

With continued reference to FIG. 2, FIG. 3 provides an enlarged elevation view of clamp member 205, which roughly forms an upside down "T" shaped prism and, thereby, includes a pair of lower protrusions 205a and 205b. Lower protrusions 205a and 205b may include respective pairs of mounting bores (of which mounting bores 205c, 205d, and 205e are illustrated) that enable clamp member 205 to be, for example, fixedly attached (e.g., detachably coupled) to base member 201 via a respective number of fasteners. As such, base member 201 may include a corresponding number of "other" mounting bores (of which mounting bores 201d and 201e are shown) that are configured to interface with the mounting bores of clamp member 205. Similarly to mounting bores 201a and 201b, the mounting bores of lower protrusions 205a and 205b may be tapered (e.g., or otherwise countersunk) from upper surfaces 215 and 217 of clamp member 205 to enable corresponding fasteners (not shown), once engaged with base member 201 and clamp member 205, to have upper surfaces that are flush (or substantially flush) with respective upper surfaces 215 and 217. The mounting bores of clamp member 205 may or may not be tapped (or threaded). According to particular embodiments, the mounting bores of clamp member 205 are not tapped and the corresponding mounting bores of base member 201 (e.g., mounting bores 201d and 201e) are tapped. Alternatively, the mounting bores of clamp member 205 may be tapped, such that the mounting bores of base member 201 are not tapped.

Clamp member 205 also includes a bore 219 in an intermediate region 221 that is configured to slidably receive telescopic member 211. An upper region 223 of clamp member 205 may include a pair of flanges 223a and 223b that extend integrally upward from intermediate region 221 and, thereby, also define a slotted region 225 therebetween. Slotted region 225 extends from an upper surface 227 of clamp member 205 into bore 219. Flanges 223a and 223b each include a pair of bores 229 and 231 that are configured to accommodate compression pin 233 and locking screw 235. Bores 229 and 231 of flange 223a may be countersunk (or otherwise recessed) from an outer surface 237 of clamp member 205. In this manner, when telescopic member 211 is slidably received by bore 219, selective adjustment of locking screw 235 via control mechanism (e.g., lever) 239 enables (or constrains) telescopic displacement of telescopic member 211, as will become more apparent below.

According to exemplary embodiments, control mechanism 239 includes handle portion 241 fixedly attached to shaft portion 243 that is, in turn, fixedly attached to engagement portion 245 that has an internally threaded bore 247. Internally threaded bore 247 is configured to interface with bore 229 of flange 223b and, thereby, with locking screw 235. As such, internally threaded bore 247 and bore 229 may be conically centered to an imaginary axis 253 parallel (or substantially parallel) to an imaginary Y axis. It is noted that an inner surface 249 of engagement portion 245 may abut an outer surface 251 of clamp member 205. In this manner, internally threaded bore 247 is configured to accept a distal end of locking screw 235, such that rotating locking screw about imaginary axis 253 via control mechanism 239 compresses flanges 223a and 223b together, thereby reducing a transverse width 255 of slotted region 225. When, for instance, locking screw 235 is sufficiently tightened, a diameter of bore 219 is reduced to rigidly fix an outer surface of telescopic member 211 against an inner surface 219a of bore 219. This tightening movement enables clamp member 205 to constrain telescopic displacement of telescopic member 211 in a direction parallel (or substantially parallel) to an imaginary X axis. It is also noted that radial displacement of telescopic member 211 with respect to bore 219 may also be constrained, as well as rotational motion about imaginary axis 257 extending in a direction parallel (or substantially parallel) to the imaginary X axis.

Compression pin 235 also acts to compress flanges 223a and 223b together and, thus, may be biased between, for instance, outer surfaces 237 and 251 of flanges 223a and 223b. As such, when locking screw 235 is tightened, compression pin 235 helps to provide consistent (or at least sufficient) compressive force on the outer surface of telescopic member 211 along the length of bore 219. When locking screw 235 is "unfastened," e.g., control mechanism 239 is rotated about imaginary axis 253 in a manner contrary to tightening locking screw 235, the pulling (or pushing apart) of flanges 223a and 223b via locking screw 235 may counteract compressive forces of compression pin 235 to enable selective displacement and/or rotation of telescopic member 211. In this manner, clamp member 205, via telescopic member 211, enables bolster pad 203 to be telescopically displaced, such as along the imaginary X axis, as well as rotated about imaginary axis 257. Further, the aforementioned arrangement also constitutes a locking mechanism configured to secure bolster pad 203 in one or more medically relevant positions.

Figure 4:
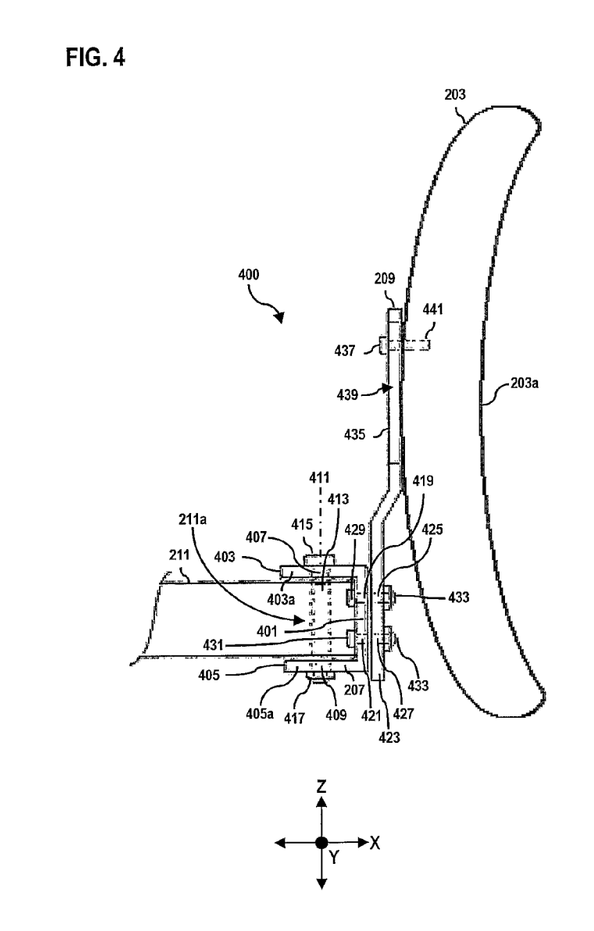
FIG. 4 is an enlarged elevation view of a distal end of a spatially configurable bolster of the patient table of FIG. 1, according to an exemplary embodiment.

Averting to FIG. 4, there is shown an enlarged elevation view of a distal end 400 of bolster 109a that, according to exemplary embodiments, supports bolster pad 203 at a free end 211a of telescopic member 211 via one or more support structures, such as first bracket 207 and second bracket 209. In exemplary embodiments, first bracket (or bracket) 207 roughly forms a backwards "C" shape and, thereby, includes a main body portion 401 and corresponding flange portions 403 and 405. Flange portions 403 and 405 may have chamfered edges (such as chamfered edges 403a and 405a), such that when flanges 403 and 405 are seen in a plan view, flanges 403 and 405 appear trapezoidal, which can also be seen in FIG. 1. Flanges 403 and 405 respectively include mounting bores 407 and 409 that are conically centered along imaginary axis 411 extending parallel (or substantially parallel) to an imaginary Z axis. In this manner, telescopic member 211 may also include a mounting bore 413 that conically aligns with imaginary axis 411 when telescopic member 211 is detachably coupled to bracket 207. As such, locking bolt 415 may be received by mounting bores 407, 413, and 409 and correspondingly secured via locking nut 417, which detachably couples telescopic member 211 to bracket 207. It is noted that locking bolt 415 and locking nut 417 may be selectively "loosened" to enable bolster pad 203 to be rotated about imaginary axis 411 and, thus, correspondingly "tightened" to enable bolster 203 to be secured in a particular position (or spatial configuration). This arrangement forms another locking mechanism of bolster 109a.

According to exemplary embodiments, main body portion 401 may include a plurality of mounting bores, such as four mounting bores, that enable bracket 207 to be detachably coupled to second bracket (or bracket) 209. It is noted that only two of these mounting bores, i.e., mounting bores 419 and 421, may be seen in FIG. 4. In certain embodiments, a first set (e.g., two) of these mounting bores may be formed along a first side of main body portion 401 and a second set (e.g., two) of these mounting bores may be formed along a second side of main body portion 401. As such, bracket 209 may include corresponding sets of mounting bores formed in a lower region 423, such as mounting bores 425 and 427. The mounting bores of main body portion 401 of bracket 207 and of lower portion 423 of bracket 209 enable brackets 207 and 209 to be detachably coupled, e.g., detachably fastened. For instance, a plurality of locking bolts (e.g., locking bolts 429 and 431) may be received by the mounting bores of brackets 207 and 209 and fastened via a corresponding plurality of locking nuts (e.g., locking nuts 433 and 435).

As seen in FIG. 4, bolster pad 203 is detachably coupled to an upper portion 435 of bracket 209 via, for instance, one or more fasteners (e.g., fastener 437). In certain instances, bracket 209 may also include one or more slotted regions (e.g., slotted region 439) formed in upper portion 435 that longitudinally extend, for example, in a direction parallel (or substantially parallel) to the imaginary Z axis. According to exemplary embodiments, any number (e.g., three) of these slotted regions 439 may be utilized and may be transversely spaced and, thereby, longitudinally parallel to one another. Slotted regions 439 may be rectilinear; however, any other suitable geometry may be utilized. As such, bolster pad 203 may include a plurality of internally threaded mounting bores (e.g., internally threaded mounting bore 441) configured to threadedly engage with a respective number of fasteners 437 received through slotted regions 439 of bracket 209. In this manner, bolster pad 203 may be detachably coupled to bracket 209 and, in turn, detachably secured to distal end 211a of telescopic member 211. It is noted that fasteners 437 may be selectively "loosened" to enable bolster pad 203 to be positioned (e.g., spatially configured) along the longitudinal length of slotted region(s) 439, e.g., in a direction parallel (or substantially parallel) to the imaginary Z axis. As such, this arrangement forms another locking mechanism of bolster 109a.

According to exemplary embodiments, an outer surface 203a of bolster pad 203 may be formed having any suitable geometry capable of interfacing with a subject to be supported via patient table 107, such as arcuately formed. Since bolster pad 203 may be utilized for supporting a subject when, for example, acquiring radiographic images of the subject, bolster pad 203 may be formed of one or more suitable radiolucent materials, e.g., one or more suitable composites, elastomers, plastics, polymers, etc. In certain embodiments, bolster pad 203 may be an inflatable, pneumatic member (e.g., balloon) capable of conforming to the idiosyncrasies of the subject (e.g., patient) being bolstered. While not illustrated, it is contemplated that bolster pad 203 may include a depressurization valve for adjusting a stiffness (or internal pressure) of bolster pad 203. Additionally, bolster pad 203 may include one or more sensors (e.g., pressure sensors), as will become more apparent below. In certain other embodiments, additional or alternative support members may be utilized in conjunction with or in place of bolster pad 203, such as one or more end effectors, e.g., clamps, cups, flanges, grippers, hooks, pledgers, etc.

Figure 5:
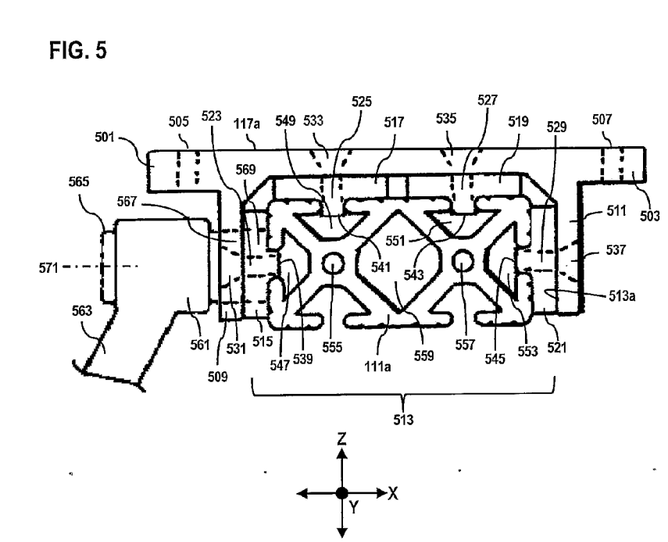
FIG. 5 is an enlarged sectional view of a guide assembly of the patient table of FIG. 1, according to an exemplary embodiment.

With continued reference to FIG. 2, FIG. 5 provides an enlarged sectional view of guide 117a interfaced with guide member 111a. As previously mentioned, the conjunction of guide 117a and guide member 111a forms a linear bearing assembly that enables translational displacement of bolster 109a along a longitudinal length (or portion thereof) of patient table 107, such as translational displacement in a direction parallel (or substantially parallel) to the imaginary Y axis that, in FIG. 5, extends out of the page. Guide 117a includes a plurality of transverse flanges 501 and 503 having a corresponding pair of mounting bores, such as mounting bores 505 and 507. The mounting bores of flanges 501 and 503 are configured to interface with the corresponding mounting bores of base member 201, such as mounting bores 201a and 201b, which enables base member 201 to be detachably coupled to guide 117a via, for example, one or more fasteners, e.g., screws, nuts, bolts, pins, washers, etc. Guide 117a also includes a pair of downwardly extending flanges 509 and 511 that form traverse boundaries of an interior cavity region 513.

A plurality of pad members, such as pad members 515, 517, 519, and 521, are detachably coupled to an inner surface 513a of interior cavity region 513 via a plurality of mounting bores (e.g., mounting bores 523, 525, 527, and 529) that are, in exemplary embodiments, threaded. As such, guide 117a includes a corresponding plurality of mounting bores, such as mounting bores 531, 533, 535, 537, that are configured to interface with the mounting bores of pad members 515-521. Mounting bores 531-537 may be tapered (or otherwise countersunk) from an outer surface of guide 117a, which enables a corresponding number of fasteners (not shown), once respectively engaged with guide 117a and pad members 515-521 via mounting bores 523-537, to have upper surfaces flush (or substantially flush) with the outer surface of guide 117a.

In exemplary embodiments, pad members 515-521 include respective protrusions 539, 541, 543, and 545 that are formed to corresponding outer surfaces of pad members 515-521 and, thereby, are configured to respectively interface with slotted channels 547, 549, 551, and 553 of guide member 111a. It is noted that pad members 515-521 may constructed of one or more low coefficient of friction materials, such as suitable polymeric materials, which may filled or reinforced with one or more particulate fillers, fiber reinforcements, etc. As such, when guide 117a is longitudinally displaced along guide member 111a, slotted channels 547-553 enable protrusions 539-545 to freely slide, for instance, in a direction parallel (or substantially parallel) to the imaginary Y axis. Engagement of protrusions 539-545 within at least a portion of slotted channels 547-553 also serves to constrain "other" forms of translational displacement of guide member 117a, such as translational displacement in directions parallel (or substantially parallel) to the imaginary X and Z axes, not to mention, constrain rotational motion of guide member 117a about the imaginary X, Y, and Z axes.

Figure 6:
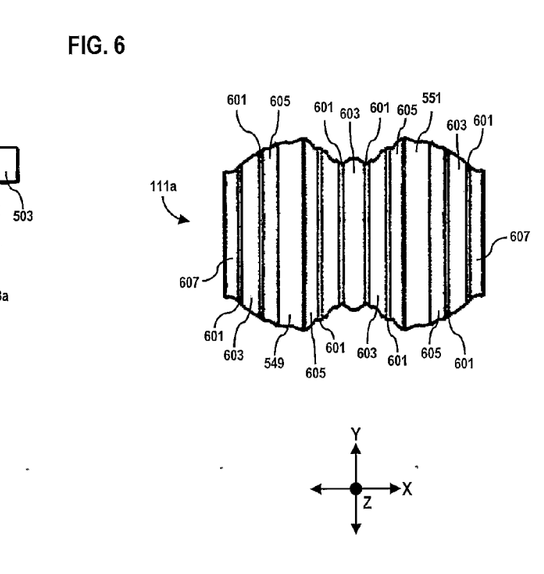
FIG. 6 is an enlarged plan view of an upper portion of a guide member of the guide assembly of FIG. 5, according to an exemplary embodiment.

With continued reference to FIG. 5, FIG. 6 provides an enlarged plan view of an upper portion of a guide member 111a. According to exemplary embodiments, guide member 111a includes a plurality of grooves 601 that separate a plurality of rails 603. Respective outer surfaces of pad members 515-521 are configured to abut against corresponding outer surfaces of rails 603. In this manner, grooves 601 may serve to reduce an amount of contact surface area between the outer surfaces of guide member 117a and pad members 515-521, which may reduce an effective coefficient of friction between guide member 111a and pad members 515-521. It is noted that interior corners 605 of slotted channels 547-553 may be rounded (or otherwise reduced), which may also be the case for exterior corners 607. Guide member 111a may further include a plurality of mounting bores (e.g., mounting bores 555 and 557) configured to enable guide member 111a to be detachably coupled to patient table 103 via, for instance, structural members 113a and 113b, which will become more apparent below. An inner cavity region 559 may be provided for routing purposes, such as for routing air lines, electrical wires, tubes, etc.

According to exemplary embodiments, guide 117a may additionally include a locking mechanism 561 having a handle portion 563 and a threaded engagement shaft 565. In this manner, flange 509 and pad member 515 respectively include threaded bores (or bores) 567 and 569 configured to receive and, thereby, interface with threaded engagement shaft 565. Bores 567 and 569 may be conically aligned to an imaginary central axis 571 that extends in a direction parallel (or substantially parallel) to the imaginary X axis. As such, when threaded engagement shaft 565 is rotated about central axis 571 via, for example, handle portion 561, a distal end of threaded engagement shaft 563 may be selectively biased against an outer surface of guide member 111a. When biased against the outer surface of guide member 111a, the distal end of threaded engagement shaft 565 serves to constrain translational displacement of guide 117a along guide member 111a. Conversely, when the distal end of threaded engagement shaft 565 is unbiased from the outer surface of guide member 111a, guide 117a may be spatially configured (e.g., linearly translated) along at least a portion of the longitudinal length of guide member 111a. It is noted that any other suitable locking mechanism may be utilized to constrain displacement of guide 117a.

Figure 7:
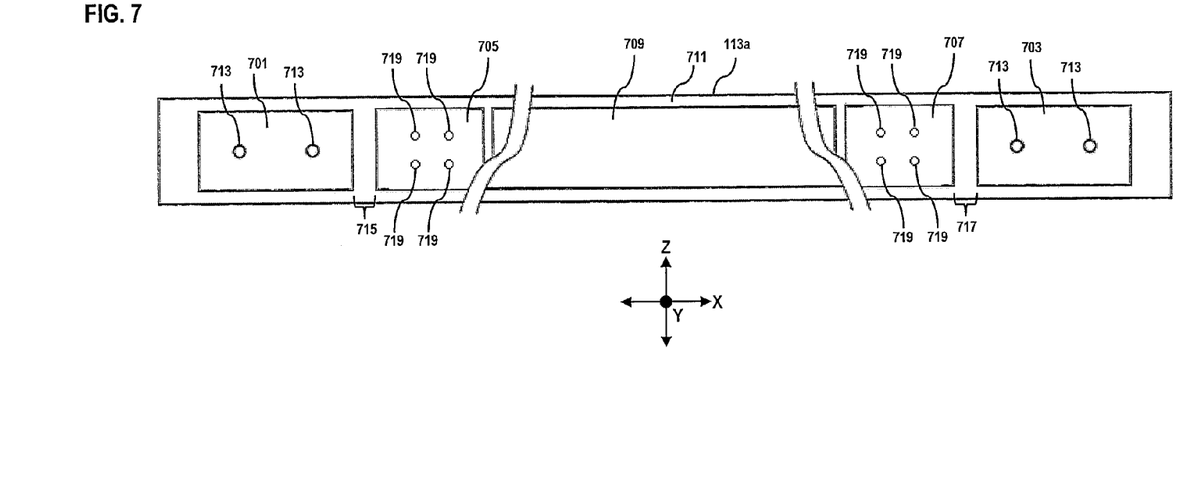
FIG. 7 is an enlarged elevation view of a structural member of the patient table of FIG. 1, according to an exemplary embodiment.

As previously mentioned, guide members 111a and 111b may be fixedly attached to patient table 103 via structural members 113a and 113b. FIG. 7 is an enlarged elevation view of structural member 113a. According to exemplary embodiments, structural member 113a includes a plurality of receiving portions, such as receiving portions 701, 703, 705, 707, and 709, which may be recessed from an inner surface 711 of structural member 113a. In this manner, receiving portions 701 and 703 may be configured to receive respective distal ends of guide members 111a and 111b that may be detachably coupled to structural member 111a via, for instance, a plurality of fasteners. As such, receiving portions 701 and 703 may include mounting bores 713 that enable the fasteners to engage with the mounting bores of guide members 111a and 111b, such as mounting bores 555 and 557. It is noted that mounting bores 713 may or may not be threaded and may or may not include tapered (or otherwise countersunk) openings.

In exemplary embodiments, receiving portions 705 and 707 are configured to receive respective distal ends of side members 115a and 115b of patient table 103. Receiving portions 705 and 703 may be transversely spaced at distances 715 and 717 in order to enable respective outer surfaces of guides 117a-117c to be spaced from respective outer surfaces of side members 115a and 115b of top member 107, which is more readily apparent in FIG. 2. For instance, outer surface 259 of guide 117a is transversely spaced from an outer surface 261 top member 107. It is noted that receiving portions 705 and 707 may also include a plurality of mounting bores 719 that are configured to receive a corresponding number of fasteners, which detachably engage with a respective number of mounting bores (not shown) of side members 115a and 115b. Accordingly, structural member 113a may be detachably coupled to patient table 103, such that a distal end of top member 107 may be received by receiving portion 709.

Averting back to FIGS. 1 and 2, it is contemplated that the spatial configuration (or positioning) of bolster pads 203 may be manually coordinated and constrained via one or more of the aforementioned components of bolsters 109a-109d and guides 117a-117d; however, it is also contemplated that diagnostic system 100 may be capable of automated configuration. That is, the spatial configuration of bolster pads 203 and, thereby, the spatial configuration of the several components of diagnostic system 100 may be wholly or partially controlled via one or more actuators, effectors, controllers, etc., which will become more apparent below. In any case, the spatial positioning of bolster pads 203 may be configured with respect to one or more degrees of freedom, such that a subject (or patient) may be correspondingly arranged and supported in a variety of medically relevant positions, such as one or more multipoint bending positions, during a medical procedure without requiring one or more individuals to physically hold the subject during the procedure.

Figure 8:
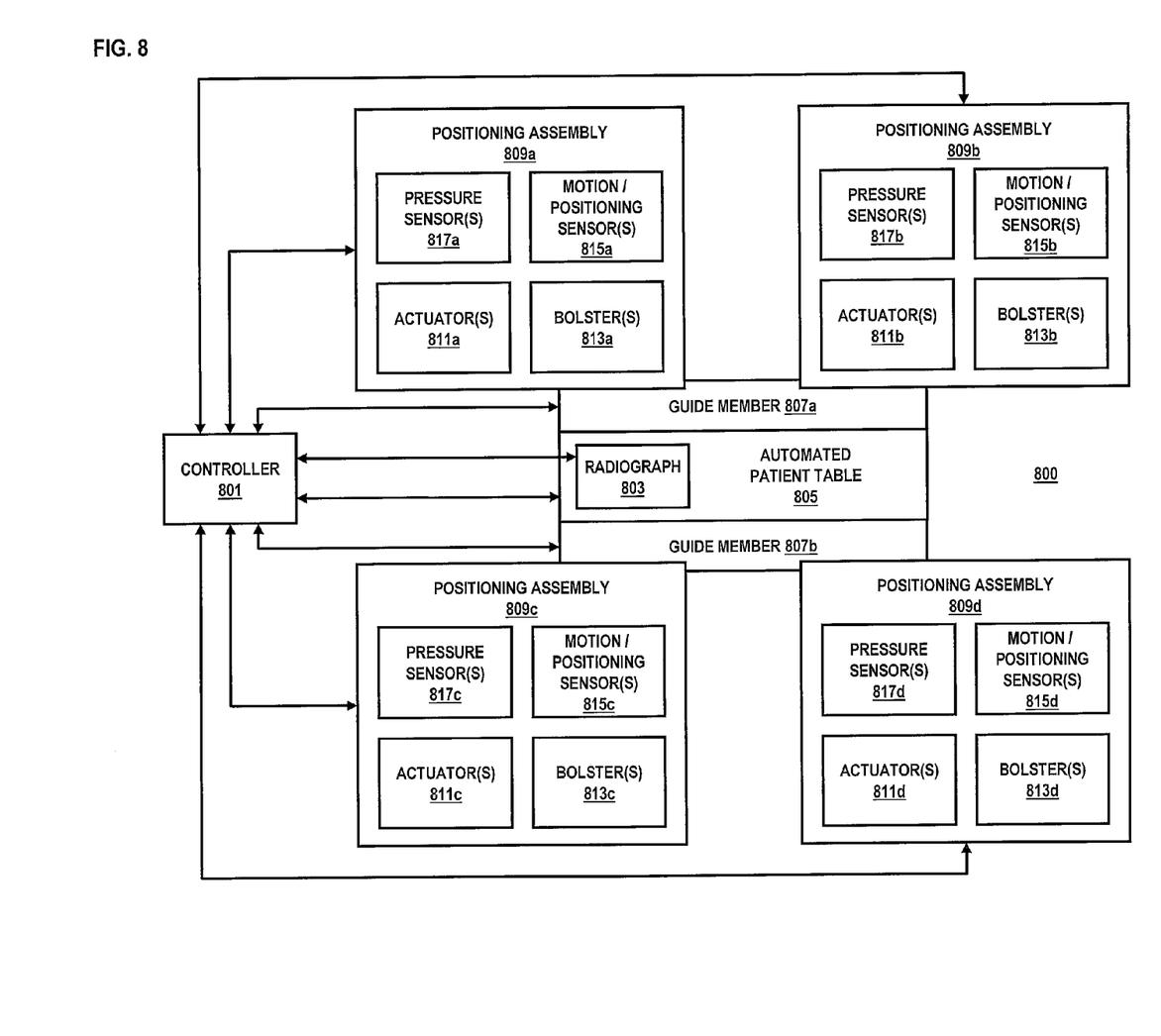
FIG. 8 is a schematic block diagram of an automated diagnostic system including an automated patient table, according to an exemplary embodiment.

FIG. 8 is a schematic block diagram of an automated diagnostic system including an automated patient table, according to an exemplary embodiment. For illustrative purposes, automated diagnostic system (or system) 800, such as an automated radiographic system, may be configured to obtain radiographic images (or radiographs) of a subject (not shown) and, thereby, may be implemented as a tool for assessing and diagnosing structural deformities, as well as numerous other conditions, whether structurally related or not. As such, system 800 may be similar to system 100 and may include, among other components, controller 801, radiograph 803, and automated patient table (or table) 805. While specific reference will be made hereto, it is contemplated that system 800 may embody many forms and include multiple and/or alternative components.

Similarly to system 100, table 805 of system 800 may include a plurality of guide members 807a and 807b that extend along at least a portion of a longitudinal length of table 805, however, it is contemplated that guide members 807a and/or 807b may extend along at least a portion of a transverse width of table 805 or any other dimension for that matter. As shown, guide members 807a and 807b extend along an entirety of the longitudinal length of automated patient table 805 and, thereby, are fixedly attached to table 805 via any suitable coupling mechanism(s). It is also contemplated that guide members 807a and 807b may be integrally formed to table 805.

According to exemplary embodiments, guide members 807a and 807b are configured to interface with and, thereby, support a plurality of positioning assemblies, such as positioning assemblies 809a, 809b, 809c, and 809d, which are configured to spatially position and support a patient (not shown) in one or more diagnostic positions, such as one or more multipoint bending positions. In order to facilitate the patient arranging and supporting functions of positioning assemblies 809a-809d, positioning assemblies 809a-809d may respectively include one or more actuators (e.g., actuators 811a, 811b, 811c, and 811d), bolsters (e.g., bolsters 813a, 813b, 813c, and 813d), and/or sensors (e.g., motion/positioning sensors 815a, 815b, 815c, and 815d, pressure sensors 817a, 817b, 817c, and 817d, etc.). Even though the several components of positioning assemblies 809a-809d are separately illustrated, it is contemplated that one or more of these components may be integrally formed and/or interfaced. An exemplary positioning assembly is described in more detail in association with FIG. 9.

Figure 9:
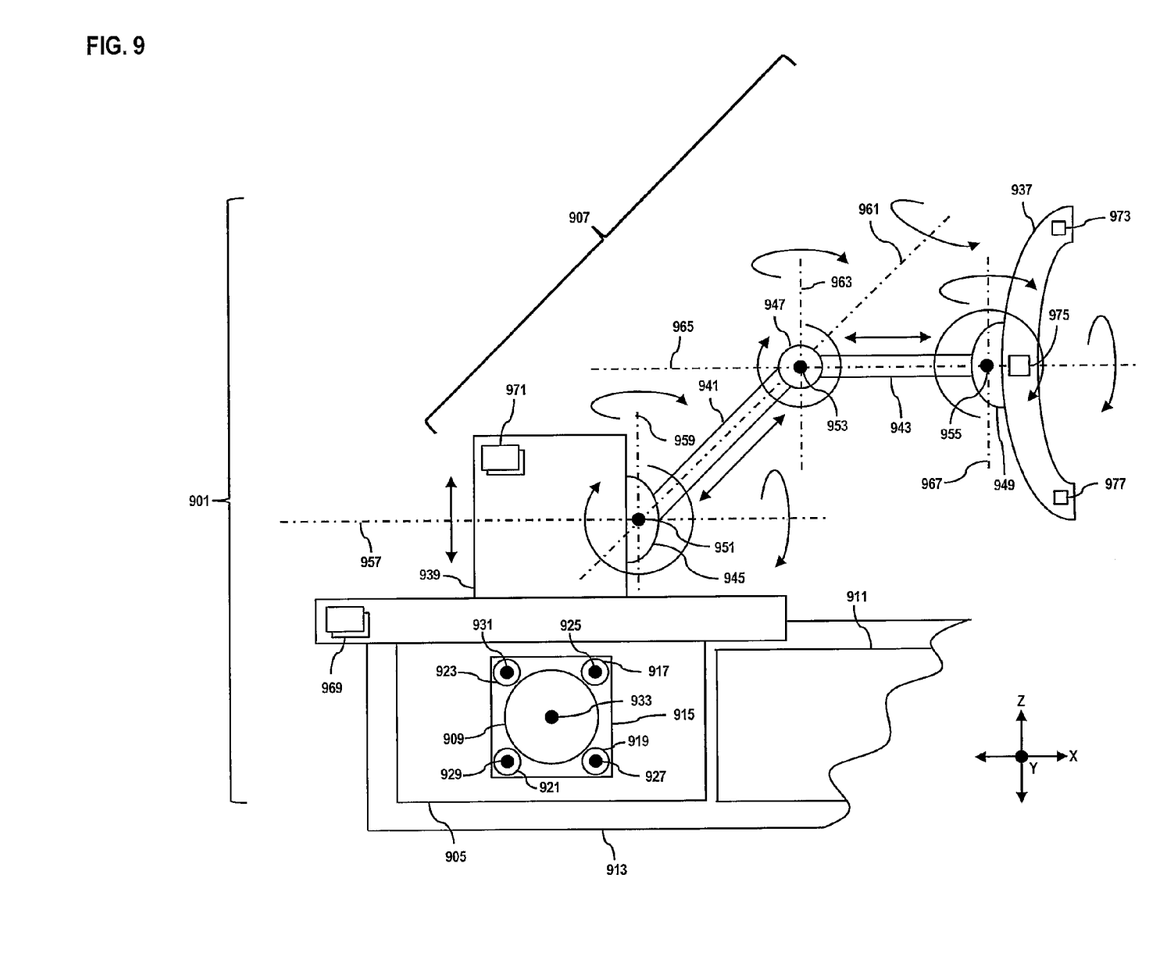
FIG. 9 is a schematic block diagram of an automated positioning assembly of the automated diagnostic system of FIG. 8, according to an exemplary embodiment.

Averting to FIG. 9, an exemplary positioning assembly 901 is shown. Accordingly to various embodiments, positioning assembly 901 includes guide 905 configured to support one or more manipulators 907, as well as interface with guide member 909. In this manner, guide member 909 may be fixedly attached to automated patient table (or table) 911 via one or more structural members, such as structural member 913, that may be fixedly attached to table 911 at, for instance, respective transverse ends of table 911. Guide 905 may include a drive region 915 that is configured to support one or more helical gears 917, 919, 921, and 923 therein that may be capable of rotational motion about imaginary axes of rotation 925, 927, 929, and 931 that extend in directions parallel (or substantially parallel) to an imaginary Y axis. Drive region 915 is also configured to receive guide member 909 that, in certain embodiments, is a helically threaded shaft that may be capable of rotational motion about imaginary axis of rotation 933. In this manner, gears 917-923 are configured to mesh with shaft 909, such that rotational motion of one or more of shaft 909 and/or gears 917-923 may be converted into translational displacement of guide 905 along at least a portion of the longitudinal length of table 911.

In exemplary embodiments, one or more bolsters 937 may be supported via manipulator(s) 907 that are capable of dynamically modifying the spatial configuration (or positioning) of bolster(s) 937. Manipulator 907 may be, for example, a kinematic chain, such as an articulated robotic arm, including one or more links (e.g., links 939, 941, and 943) connected via one or more joints (e.g., joints 945, 947, and 949). As such, links 939-943 and joints 945-949 enable various forms of rotational motion and/or translational displacement, such as dynamically rotating and/or translating bolster 937 relative an imaginary X, Y, and/or Z axis in order to arrange a subject (not shown) in one or more diagnostic positions, such as one or more multipoint bending positions. For instance, links 941 and 943, as well as joints 945-949 may enable bolster 937 to rotate about imaginary axes of rotation 951, 953, and 955 that, in the illustrated embodiment, are parallel (or substantially parallel) to the imaginary Y axis extending out of the page, as well as rotate about imaginary axes of rotation 957, 959, 961, 963, 965, 967 that, in the illustrated embodiment, are respectively parallel (or substantially parallel) to either an imaginary X axis, imaginary Z axis, or imaginary axis therebetween. Moreover, links 939-943 may enable bolster 937 to be displaced in one or more directions parallel (or substantially parallel) to the imaginary X, Y, and Z axes, as well as in one or more directions therebetween. It is noted that these rotational motions and translational displacements are relative to the illustrated embodiment and, therefore, as positioning assembly 901 is spatially configured, these rotational motions and translational displacements will correspondingly be modified. Thus, it is contemplated that links 939-943 and joints 945-949 enable bolster 937 to be spatially configured with respect to one or more degrees of freedom. While only a certain number of links and joints are depicted, it is contemplated that any suitable number may be utilized that are capable of various additional (or alternative) degrees of freedom.

Referring also to FIG. 8, controller 801 may be configured to impart the rotational motion and/or translational displacement of guide 905, shaft 909, gears 917-923, links 939-943, and/or joints 945-949 in (or during) one or more "stages" of arranging a subject in a diagnostic position, such as in a multipoint bending position. More specifically, controller 801 may control these components via one or more actuators 811a-811d according to one or more programs, instructions, and/or data stored to, for example, a memory (not shown) of controller 801 and/or a database (not illustrated) accessible to controller 801. Actuators 811a-811d may include any suitable means for modifying the spatial configuration of the various components of system 800, such as suitable belt drives, comb drives, electroactive polymers, hydraulic mechanisms, motors, pistons, piezoelectric mechanisms, pneumatic mechanisms, relays, step motors, telescopic members, thermal bimorphs, and the like, as well as combinations thereof. With respect to positioning assembly 901, actuators (such as actuators 811a-811d) may be disposed or otherwise distributed in any suitable manner, such as along (or at) the various components of manipulator(s) 907, guide 905, and/or guide member 909.

In certain instances, input from one or more sensors 815a-815d, 817a-817d, 969, 971, 973, 975, and 977 (or other suitable feedback mechanisms) may be provided to controller 801 to monitor and facilitate automated spatial configuration (e.g., positioning) of bolster 937, as well as to facilitate automating other aspects related to performing a diagnostic procedure via system 800, such as obtaining one or more radiographic images (e.g., "bending films") for assessing, diagnosing, and/or planning treatment related to idiopathic scoliotic curves. With respect to positioning assembly 901, sensors 969 and 971 may relate to motion and/or positioning sensors 815a-815d, whereas sensors 973-977 may relate to pressure sensors 817a-817d. Further, these sensors may be disposed or otherwise distributed in any suitable manner, such as along (or at) the various components of manipulator(s) 907, guide 905, and/or guide member 909. As such, sensed conditions (or other feedback information) may be provided to controller 801 for controlling the components of system 800, as well as may be stored to the previously mentioned memory of controller 801 and/or database accessible to controller 801. As such, exemplary embodiments enable various components of system 800 to be spatially (or otherwise) configured and, thus, enable positioning assemblies, such as positioning assemblies 809a-809d, to arrange and support a subject (or patient) in one or more diagnostic positions, such as one or more multipoint bending positions. It is noted that an exemplary controller is more fully described in association with FIG. 10.

Figure 10:
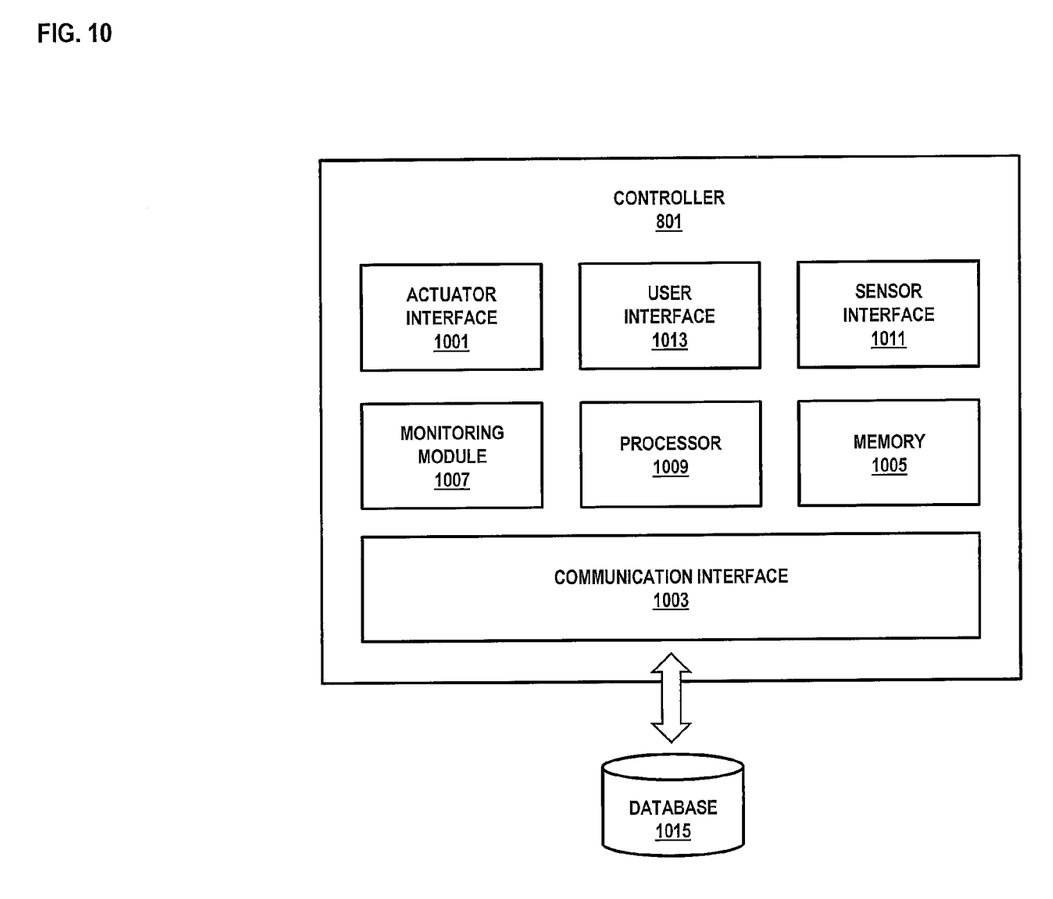
FIG. 10 is a schematic block diagram of the controller of the automated diagnostic system of FIG. 8, according to an exemplary embodiment.

FIG. 10 is a schematic block diagram of controller 801, according to an exemplary embodiment. Controller 801 may comprise computing hardware (such as described with respect to FIG. 12), as well as include one or more components configured to execute the processes described herein for automated arrangement and support of a subject (or patient) in one or more diagnostic positions, such as one or more multipoint bending positions. In one implementation, controller 801 may include one or more actuator interfaces 1001, communication interfaces 1003, memories 1005, monitoring modules 1007, processors 1009, sensor interfaces 1011, and/or user interfaces 1013. Controller 801 may also communicate with one or more databases, such as database 1015. Users (such as radiographic technicians, doctors, administrators, etc.) may access the features and functionality of controller 801 via any suitable client device (not shown), such as any wired or wireless computing device. While specific reference will be made to this particular implementation, it is also contemplated that controller 801 may embody many forms and include multiple and/or alternative components. For example, it is contemplated that the components of controller 801 may be combined, located in separate structures, or even separate locations.

According to exemplary embodiments, actuator interface 1001 is configured to exchange control and/or feedback information (e.g., instructions, parameters, signals, etc.) with actuators 811a-811d. Likewise, sensor interface 1011 is configured to exchange control and/or feedback information with sensors 815a-815d and 817a-817d. In this manner, feedback information may be provided to monitoring module 1007 for monitoring the arrangement of a subject (or patient) via positioning assemblies 809a-809d, as well as for monitoring one or more other aspects related to supporting the subject, e.g., applied pressure, etc. Accordingly, processor 1009 may dynamically manage the spatial configuration of positioning assemblies 809a-809d, or one or more of the other aspects related to performing a diagnostic procedure (e.g., obtaining one or more "bending films" via radiograph 803), based on one or more programs, instructions, and/or data stored to or provided by, for example, memory 1005, monitoring module 1007, and/or database 1009. In exemplary embodiments, the physical configurations of positioning assemblies 809a-809d are referred to as states; accordingly, a change in physical configuration with respect to positioning assemblies 809a-809d are considered changes in states. In this manner, monitoring module 1007 can monitor these states and can record corresponding information to memory 1005 and/or database 1009 for tracking, optimizing, or otherwise controlling the various components of system 800.

It is noted that control and feedback information (e.g., instructions, parameters, signals, data, etc.) for configuring positioning assemblies 809a-809d may be stored to memory 1005, e.g., any non-volatile memory, such as erasable programmable read-only memory (EPROM), electrically erasable programmable read-only memory (EEPROM), and/or flash memory, as well as any other suitable storage location, e.g., database 1009. Memory 1005 may be implemented as one or more discrete devices, stacked devices, or integrated with processor 1009 and/or database 1009. Memory 1005 may represent a hierarchy of memory, which may include both random access memory (RAM) and read-only memory (ROM). Further, control functions may be implemented via processor 1009, which may be a single processor or multiple processors. Suitable processors 1009 may include, for example, both general purpose and special purpose processors, such as one or more digital signal processors.

According to certain embodiments, controller 801 may configured to receive control and configuration information over one or more communication networks (not shown) for dynamically controlling patient positioning and/or any other suitable aspect of performing a diagnostic procedure via system 800 (e.g., dynamically controlling positioning assemblies 809a-809d, table 805, and/or one or more of the other aspects of, for instance, radiographic imaging via radiograph 803) and, thereby, may include communication interface 1003 and/or user interface 1013 for receiving this control and/or configuration information. Suitable communication networks, whether wired or wireless, may include local area networks (LAN), metropolitan area networks (MAN), wide area networks (WAN), the Internet, etc. In this manner, user interface 1013 may be configured to provide one or more client programs, e.g., graphical user interfaces (GUI), configured to provide users with one or more menus of options for interacting with the various functions of controller 801 and, thereby, the various components of diagnostic system 800.

Figure 11:
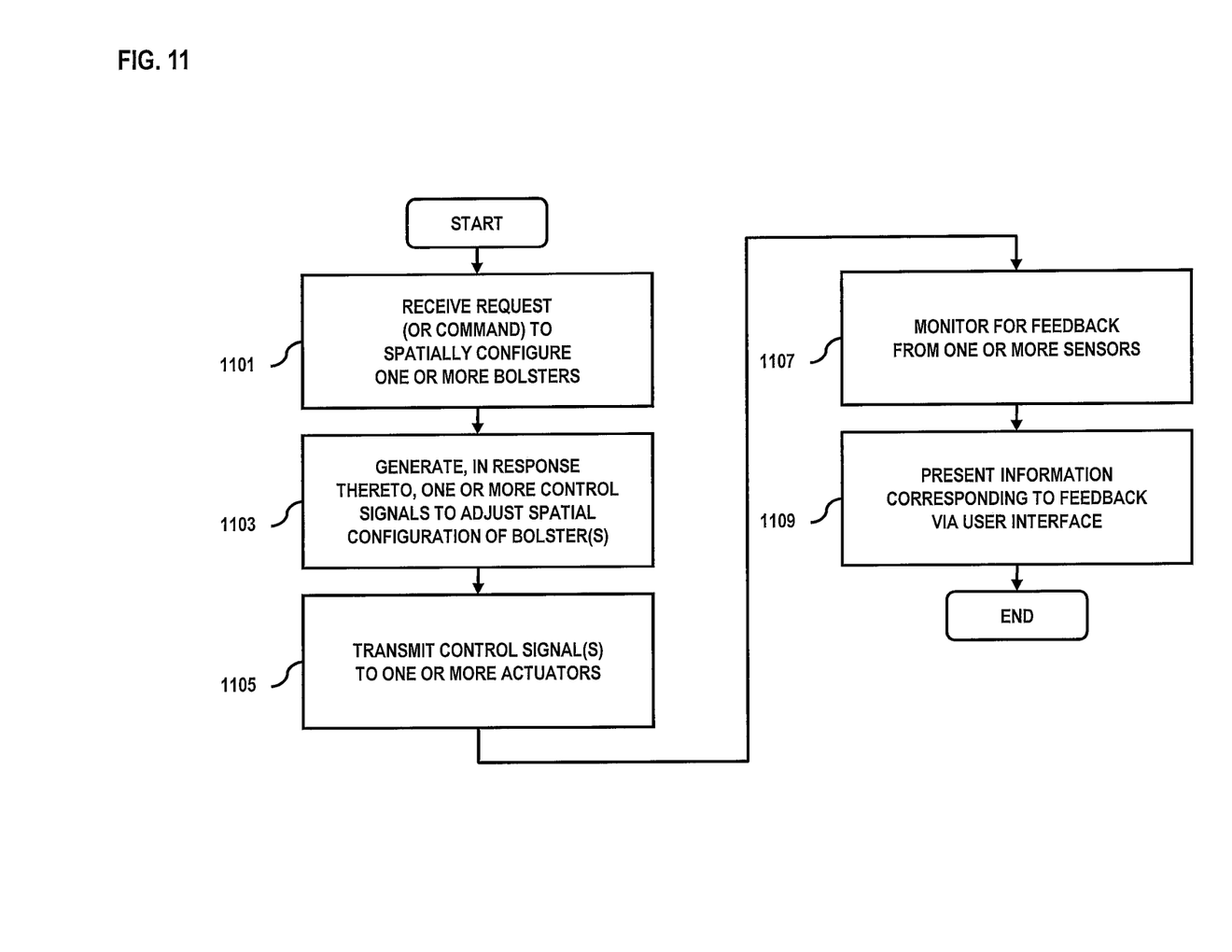
FIG. 11 is a flowchart of a process for arranging a patient in a medically relevant position, according to an exemplary embodiment.

FIG. 11 is a flowchart of a process for arranging a patient in a medical position, according to an exemplary embodiment. For illustrative purposes, the process is described with respect to FIGS. 8 and 10. It is noted that the steps of the process may be performed in any suitable order, as well as combined or separated in any suitable manner. In step 1101, controller 801 receives a request(s) or (one or more commands) to spatially configure one or more bolsters 813a-813d to support a subject (or patient) in a diagnostic position, such as a multipoint bending position (e.g., a three-point bending position), on table 805 during a medical procedure, such as a radiographic imaging procedure. It is noted that table 805 has one or more positioning assemblies 809a-809d that correspondingly include bolsters 813a-813d. Further, the request(s) or command(s) may be received and/or acquired from memory 1005 and/or database 1015, and, additionally (or alternatively) over one or more of the aforementioned communication networks. Per step 1103, controller 801, in response to the request(s) or command(s), generates one or more control signals to adjust a spatial configuration of bolsters 813a-813d via, for example, actuator interface 1001. In step 1105, controller 801 via, for instance, actuator interface 1001 and communication interface 1003 transmits the control signal(s) to one or more actuators 811a-811d configured to effectuate physical movement of bolsters 813a-813d according to the one or more control signals. That is, controller 801 provides control signal(s) to actuators 811a-811d that manipulate (e.g., extend, rotate, or retract) bolsters 813a-813d into the intended spatial configuration. These control signals may be, in exemplary embodiments, derived based on optimization or calibration information stored to, for example, memory 1005, database 1015, or any other suitable memory or storage location of or accessible to controller 801. In this manner, controller 801 via positioning assemblies 809a-809d is capable of automated arrangement of a subject in an intended position, which may be maintained by positioning assemblies 809a-809d during a medical procedure. Thus, at least with obtaining radiographic images, positioning assemblies 809a-809d enable the patient to be held in the desired position without unnecessarily exposing other personnel to undue radiation.

In certain embodiments, controller 801 may also monitor (at step 1107) for feedback from one or more sensors (e.g., sensors 815a-815d, 817a-817d, etc.) via, for instance, monitoring module 1007. As such, user interface 1013 may be configured to present information corresponding to the feedback via, for example, one or more graphical user interfaces, per step 1109. For instance, receiving and presenting pressure information corresponding to a pressure condition relating to respective pressures of bolsters 813a-813d against a body of a subject may enable doctors to better evaluate and diagnose curve flexibility (or elasticity) of a structural deformity, as well as treat these conditions. Receiving and presenting positioning or motion information corresponding to respective spatial configurations of bolsters 813a-813d ensures the patient is optimally positioned for the intended procedure. Furthermore, this pressure and/or positioning information may be utilized to ensure the subject is not unnecessarily injured by excessive pressures or otherwise harmful positions.

The processes described herein for providing a patient positioning mechanism may be implemented via software, hardware (e.g., general processor, Digital Signal Processing (DSP) chip, an Application Specific Integrated Circuit (ASIC), Field Programmable Gate Arrays (FPGAs), etc.), firmware or a combination thereof. Such exemplary hardware for performing the described functions is detailed below.

Figure 12:
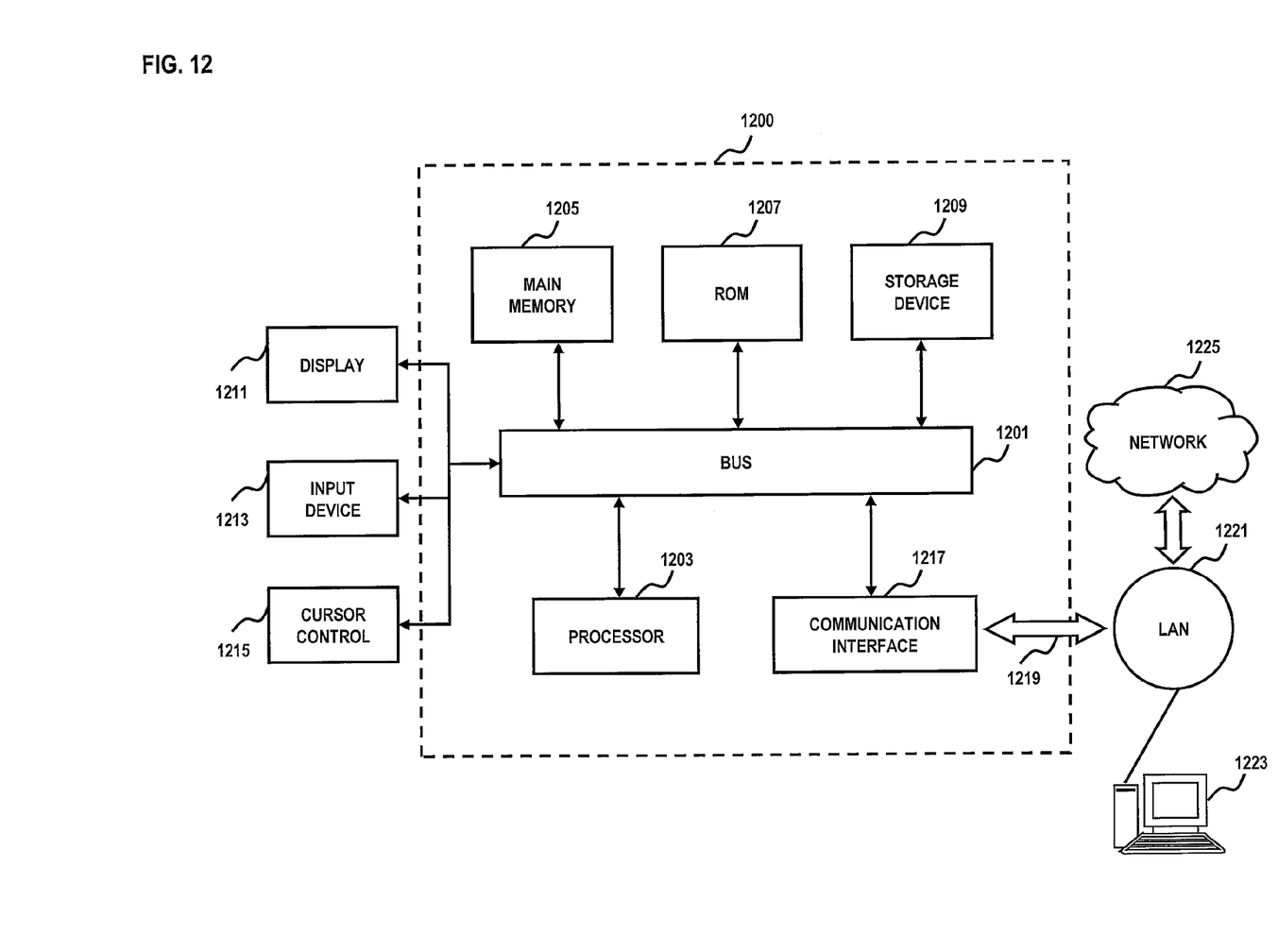
FIG. 12 is a diagram of a computer system that can be used to implement various exemplary embodiments.

FIG. 12 illustrates computing hardware (e.g., computer system) 1200 upon which exemplary embodiments can be implemented. The computer system 1200 includes a bus 1201 or other communication mechanism for communicating information and a processor 1203 coupled to the bus 1201 for processing information. The computer system 1200 also includes main memory 1205, such as a random access memory (RAM) or other dynamic storage device, coupled to the bus 1201 for storing information and instructions to be executed by the processor 1203. Main memory 1205 can also be used for storing temporary variables or other intermediate information during execution of instructions by the processor 1203. The computer system 1200 may further include a read only memory (ROM) 1207 or other static storage device coupled to the bus 1201 for storing static information and instructions for the processor 1203. A storage device 1209, such as a magnetic disk or optical disk, is coupled to the bus 1201 for persistently storing information and instructions.

The computer system 1200 may be coupled via the bus 1201 to a display 1211, such as a cathode ray tube (CRT), liquid crystal display, active matrix display, or plasma display, for displaying information to a computer user. An input device 1213, such as a keyboard including alphanumeric and other keys, is coupled to the bus 1201 for communicating information and command selections to the processor 1203. Another type of user input device is a cursor control 1215, such as a mouse, a trackball, or cursor direction keys, for communicating direction information and command selections to the processor 1203 and for controlling cursor movement on the display 1211.

According to an exemplary embodiment, the processes described herein are performed by the computer system 1200, in response to the processor 1203 executing an arrangement of instructions contained in main memory 1205. Such instructions can be read into main memory 1205 from another computer-readable medium, such as the storage device 1209. Execution of the arrangement of instructions contained in main memory 1205 causes the processor 1203 to perform the process steps described herein. One or more processors in a multi-processing arrangement may also be employed to execute the instructions contained in main memory 1205. In alternative embodiments, hard-wired circuitry may be used in place of or in combination with software instructions to implement exemplary embodiments. Thus, exemplary embodiments are not limited to any specific combination of hardware circuitry and software.

The computer system 1200 also includes a communication interface 1217 coupled to bus 1201. The communication interface 1217 provides a two-way data communication coupling to a network link 1219 connected to a local network 1221. For example, the communication interface 1217 may be a digital subscriber line (DSL) card or modem, an integrated services digital network (ISDN) card, a cable modem, a telephone modem, or any other communication interface to provide a data communication connection to a corresponding type of communication line. As another example, communication interface 1217 may be a local area network (LAN) card (e.g. for Ethernet™ or an Asynchronous Transfer Model (ATM) network) to provide a data communication connection to a compatible LAN. Wireless links can also be implemented. In any such implementation, communication interface 1217 sends and receives electrical, electromagnetic, or optical signals that carry digital data streams representing various types of information. Further, the communication interface 1217 can include peripheral interface devices, such as a Universal Serial Bus (USB) interface, a PCMCIA (Personal Computer Memory Card International Association) interface, etc. Although a single communication interface 1217 is depicted in FIG. 12, multiple communication interfaces can also be employed.

The network link 1219 typically provides data communication through one or more networks to other data devices. For example, the network link 1219 may provide a connection through local network 1221 to a host computer 1223, which has connectivity to a network 1225 (e.g. a wide area network (WAN) or the global packet data communication network now commonly referred to as the "Internet") or to data equipment operated by a service provider. The local network 1221 and the network 1225 both use electrical, electromagnetic, or optical signals to convey information and instructions. The signals through the various networks and the signals on the network link 1219 and through the communication interface 1217, which communicate digital data with the computer system 1200, are exemplary forms of carrier waves bearing the information and instructions.

The computer system 1200 can send messages and receive data, including program code, through the network(s), the network link 1219, and the communication interface 1217. In the Internet example, a server (not shown) might transmit requested code belonging to an application program for implementing an exemplary embodiment through the network 1225, the local network 1221 and the communication interface 1217. The processor 1203 may execute the transmitted code while being received and/or store the code in the storage device 1209, or other non-volatile storage for later execution. In this manner, the computer system 1200 may obtain application code in the form of a carrier wave.

The term "computer-readable medium" as used herein refers to any medium that participates in providing instructions to the processor 1203 for execution. Such a medium may take many forms, including but not limited to non-volatile media, volatile media, and transmission media. Non-volatile media include, for example, optical or magnetic disks, such as the storage device 1209. Volatile media include dynamic memory, such as main memory 1205. Transmission media include coaxial cables, copper wire and fiber optics, including the wires that comprise the bus 1201. Transmission media can also take the form of acoustic, optical, or electromagnetic waves, such as those generated during radio frequency (RF) and infrared (IR) data communications. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, and EPROM, a FLASH-EPROM, any other memory chip or cartridge, a carrier wave, or any other medium from which a computer can read.

Various forms of computer-readable media may be involved in providing instructions to a processor for execution. For example, the instructions for carrying out at least part of the exemplary embodiments may initially be borne on a magnetic disk of a remote computer. In such a scenario, the remote computer loads the instructions into main memory and sends the instructions over a telephone line using a modem. A modem of a local computer system receives the data on the telephone line and uses an infrared transmitter to convert the data to an infrared signal and transmit the infrared signal to a portable computing device, such as a personal digital assistant (PDA) or a laptop. An infrared detector on the portable computing device receives the information and instructions borne by the infrared signal and places the data on a bus. The bus conveys the data to main memory, from which a processor retrieves and executes the instructions. The instructions received by main memory can optionally be stored on storage device either before or after execution by processor.

While certain exemplary embodiments and implementations have been described herein, other embodiments and modifications will be apparent from this description. Accordingly, the invention is not limited to such embodiments, but rather to the broader scope of the presented claims and various obvious modifications and equivalent arrangements.

What is claimed is:

1. An apparatus comprising:
a table having a tabletop configured to support a patient thereon; and
a positioning assembly coupled to the table, the positioning assembly including:
a plurality of spatially configurable members,
a first guide member extending along at least a portion of a first side of the tabletop; and
a second guide member extending along at least a portion of a second side of the tabletop,
wherein at least some of the plurality of spatially configurable members interface with the first guide member and at least some of the plurality of spatially configurable members interface with the second guide member;
at least one guide configured to support at least one of the plurality of spatially configurable members,
wherein the at least one spatially configurable member interfaces with either the first guide member or the second guide member via the least one guide,
wherein the at least one guide is slidably engaged with either the first guide member or the second guide member and is configured to enable the at least one spatially configurable member to be selectively displaced along at least a portion of the guide member with which it is engaged,
a first locking mechanism configured to selectively constrain displacement of the at least one guide along either the first or second guide member;
a clamp member coupled to the at least one guide, the clamp member having a bore for receiving the at least one spatially configurable member and configured to enable the at least one spatially configurable member to be selectively telescopically displaced in a first direction, the clamp member including,
a second locking mechanism configured to selectively constrain a diameter of the bore to selectively constrain telescopic displacement of the at least one spatially configurable member in a first direction and selectively constrain rotational motion of the at least one spatially configurable member about an axis extending in a direction parallel to the first direction; and
wherein the positioning assembly, via the plurality of spatially configurable members, is configured to support the patient in a multipoint bending position during a medical procedure.

2. An apparatus according to claim 1, wherein at least some of the plurality of spatially configurable members are spatially configurable with respect to one or more degrees of freedom.

3. An apparatus according to claim 1, wherein the at least one clamp member is fixedly mounted to the at least one guide.

4. An apparatus according to claim 3, wherein the at least clamp member includes,
a pair of flanges defining the bore;
and wherein the locking mechanism includes a compression pin and locking screw and a lever, wherein the lever is configured to selectively constrain the diameter of the bore by adjusting the locking screw.

5. An apparatus according to claim 4, wherein the at least one guide is configured to enable the at least one spatially configurable member to be selectively displaced at any location along at least a portion of the first guide member or the second guide member.

6. An apparatus according to claim 5, wherein the at least one guide is configured to enable the at least one spatially configurable member to be selectively telescopically displaced in a first direction, and wherein the positioning assembly further includes:
   a first locking mechanism configured to selectively constrain displacement of the at least one guide along either the first or second guide member;
   a second locking mechanism configured to selectively constrain telescopic displacement of the at least one spatially configurable member in a first direction; and
   a third locking mechanism configured to selectively constrain telescopic displacement of the at least one spatially configurable member in a second direction.

7. An apparatus according to claim 1, wherein at least one of the spatially configurable members includes one or more pressure sensors configured to obtain pressure information corresponding to the multipoint bending position.

8. An apparatus according to claim 7, further comprising a controller in communication with the one or more sensors and configured to receive and monitor the pressure information corresponding to the multipoint bending position.

9. An apparatus according to claim 1, wherein the multipoint bending position is a three-point or a four-point bending position.

10. An apparatus according to claim 1, wherein the plurality of spatially configurable members comprise radiolucent materials.

11. An apparatus according to claim 1, wherein the plurality of spatially configurable members each include one or more bolster pads.

12. An apparatus according to claim 1, wherein the table is an existing table and the positioning assembly is configured to be retrofitable to the existing table.

13. A radiographic system comprising the apparatus of claim 1.

14. An apparatus comprising:
   a table having a tabletop configured to support a patient thereon; and
   a positioning assembly coupled to the table, the positioning assembly including:
      a plurality of spatially configurable members,
      a first guide member extending along at least a portion of a first side of the tabletop; and
      a second guide member extending along at least a portion of a second side of the tabletop,
         wherein at least some of the plurality of spatially configurable members interface with the first guide member and at least some of the plurality of spatially configurable members interface with the second guide member;
      at least one guide configured to support at least one of the plurality of spatially configurable members,
         wherein the at least one spatially configurable member interfaces with either the first guide member or the second guide member via the least one guide,
         wherein the at least one guide is slidably engaged with either the first guide member or the second guide member and is configured to enable the at least one spatially configurable member to be selectively displaced along at least a portion of the guide member with which it is engaged,
         wherein the at least one guide includes a base member that is disposed along a top surface of either the first guide member or the second guide member and includes a first locking mechanism configured to selectively constrain displacement of the at least one guide along either the first or second guide member, the first locking mechanism being located along an outermost end of the base member, the at least one guide further having a clamp member fixedly attached to a top surface of the base member resulting in the clamp member and the base member moving in unison when the base member is slidingly moved, the clamp member being disposed directly above either the first guide member or the second guide member, the clamp member having a bore for receiving the at least one spatially configurable member and configured to enable the at least one spatially configurable member to be selectively telescopically displaced, the clamp member including a second locking mechanism configured to selectively constrain telescopic displacement of the at least one spatially configurable member and selectively constrain rotational motion of the at least one spatially configurable member; and
      wherein the positioning assembly, via the plurality of spatially configurable members, is configured to support the patient in a multipoint bending position during a medical procedure.

* * * * *